United States Patent [19]

Ferro et al.

[11] Patent Number: 4,665,092

[45] Date of Patent: May 12, 1987

[54] STYRENE DERIVATIVES, THEIR USE AS ANTIALLERGIC AGENTS AND INTEMEDIATE EPOXIDES FOR THEIR SYNTHESIS

[75] Inventors: Michael P. Ferro, Somerville; Michael P. Wachter, Bloomsbury, both of N.J.

[73] Assignee: Ortho Pharmaceutical Corporation, Raritan, N.J.

[21] Appl. No.: 783,976

[22] Filed: Oct. 3, 1985

[51] Int. Cl.[4] .................. A61K 31/35; A61K 31/235; C07D 309/10; C07C 147/10

[52] U.S. Cl. .................................. 514/459; 514/460; 514/538; 514/708; 514/713; 549/419; 549/423; 549/414; 560/12; 560/16; 568/37; 568/45; 568/46; 568/55

[58] Field of Search .................. 549/419, 423; 560/12, 560/16; 568/37, 45, 46, 55; 514/459, 460, 538, 708, 713

[56] References Cited

PUBLICATIONS

Science, "The Leukotriences in Allergy and Inflammation", vol. 215, 12 Mar. 1982, p. 1380-1383.
Chest, "Leukotriences and Other Lipid Mediators of Asthma", Robert A. Lewis, M.D., vol. 87, No. 1 Jan. 1985, p. 5S-10S.
Drugs, "Leukotriences in Disease Implications for Drug Development", G. A. Higgs and S. Moncada, vol. 30, (1985), p. 1-5.
ACTA Physiologica Scandinavica, "Pulmonary Effects of Leukotrienes", Sven-Erik Dahlen, Stockholm 1983, Supplementum 512, p. 4-6 and 37-38.

Primary Examiner—Nicky Chan
Attorney, Agent, or Firm—David J. Levy

[57] ABSTRACT

Alkenes of the formula (I) and epoxides (II) used to make them are useful as anti-inflammatory and antiallergic pharmaceuticals:

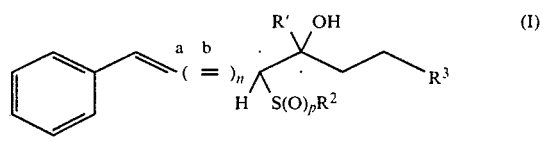

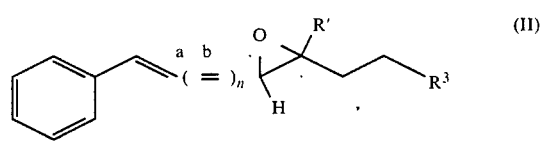

wherein $R^1 =$ H or $CH_3$; $R^2 =$ phenyl, substituted phenyl, benzyl or a cysteinyl moiety; $R^4$ and $R^5 =$ alkyl; $n =$ 0 or 1; and $R^3$ is as described.

27 Claims, No Drawings

STYRENE DERIVATIVES, THEIR USE AS ANTIALLERGIC AGENTS AND INTEMEDIATE EPOXIDES FOR THEIR SYNTHESIS

The present invention relates to alkene compounds which may be used to treat allergic reactions and inflammation in mammals, e.g. in humans. A particular mechanism of action for the compounds of the invention is the inhibition of the enzyme 5-lipoxygenase, although other mechanisms may be present. 5-Lipoxygenase is critical in the lipoxygenase pathway of arachidonic acid metabolism which produces the leukotrienes. Leukotrienes are major constituents of the slow-reacting substance of anaphylaxis (SRS-A) whose role in allergy and inflammation is described in Science, Vol. 215, Mar. 12, 1982, pages 1380–1383. SRS-A antagonists are described in U.S. Pat. No. 4,513,005.

SUMMARY OF THE INVENTION

Styrene derivatives of the formula (I):

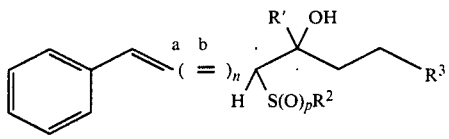

for treating allergies and inflammation where $R^1$, $R^2$ and $R^3$ are as defined herein and the configuration of the double bond or bonds is as described. The derivatives are made from the corresponding epoxides which are themselves active anti-allergic and anti-inflammatory agents.

DETAILED DESCRIPTION OF THE INVENTION

The alkenes of the present invention are of the following formula (I):

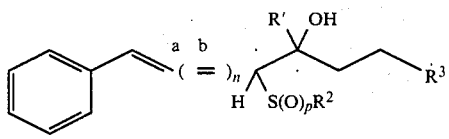

wherein
$R^1$ is hydrogen or methyl;
$R^2$ is phenyl, halogen-substituted phenyl, benzyl or —$CH_2CH(COOR^4)NHR^7$;
$R^3$ is —$CH_2CH_2OH$, —$CH_2CH_2O$(2-tetrahydropyranyl), —$CH=C(CH_3)_2$ or —$CH(OR^5)_2$
$R^4$ is lower alkyl;
$R^5$ is lower alkyl;
$R^7$ is lower alkanoyl;
n is 0 or 1;
a is a Z or E double bond when n is 0 and when n is 1, a is E;
b is a Z or E double bond;
p is 0 or 1; and
The two carbon atoms designated by an asterisk (*) are of the opposite RS configurations.

In more detail, $R^2$ is phenyl; phenyl substituted by at least one halogen such as fluoro, chloro, bromo or iodo, e.g. 2-, 3- or 4-halophenyl; benzyl; or —$CH_2CH_2$-$(COOR^4)$—NHAc. "Lower alkyl" as used herein is straight or branched alkyl of 1 to 4 carbons, e.g. methyl, ethyl or propyl, while "lower alkanoyl" is straight or branched alkanoyl of 2 to 4 carbons, e.g. acetyl or propionyl.

Particular aspects of the compounds of formula (I) are those wherein $R^2$ is phenyl; $R^3$ is —$CH_2CH_2O$(2-tetrahydropyranyl) or —$CH=C(CH_3)_2$; n is 0; and p is 0. Particularly active compounds of the invention are those of Examples 1g and 7. Specific compounds of formula (I) are the following:
(3R,4S)-4-hydroxy-1-phenyl-3-phenylthio-8-(2-tetrahydropyranyloxy)-1(E)-octene,
(5R,6S)-5-(4-chlorophenylthio)-6,10-dimethyl-6-hydroxy-1-phenylundeca-(1E,3Z,9)-triene,
methyl N-acetyl-S-3-[(3R,4S)-4-hydroxy-1-phenyl-8-(2-tetrahydropyranyloxy)-1(Z)-octenyl]-(R)-cysteinate,
methyl N-acetyl-S-3-[(3R,4S)-4,8-dihydroxy-1-phenyl-1(Z)-octenyl]-(R)-cysteinate,
(3R,4S)-1-phenyl-3-phenylthio-1(E)-octen-4,8-diol,
methyl N-acetyl-S-3-[(5R,6S)-1-phenyl-6-hydroxy-6,10-dimethylundeca-(1E,3Z,9)-trienyl]-(R)-cysteinate,
(5R,6S)-1-phenyl-5-phenylthio-6-hydroxy-6,10-dimethylundeca-(1E,3Z,9)-triene,
(3R,4S)-4-hydroxy-1-phenyl-3-phenylthio-8-(2-tetrahydropyranyloxy)-1(Z)-octene,
(3R,4S)-1-phenyl-3-phenylthio-1(Z)-octen-4,8-diol,
(3R,4S)-4-hydroxy-1-phenyl-3-phenylsulfinyl-8-(2-tetrahydropyranyloxy)-1(E)-octene,
methyl N-acetyl-S-3-[(3R,4S)-1-phenyl-4-hydroxy-4,8-dimethylnona-1(Z)-7-dienyl]-(R)-cysteinate,
(5RS,6SR)-9,9-dimethoxy-6-hydroxy-6-methyl-1-phenyl-5-phenylthio-(1E,3Z)-nonadiene,
(5R,6S)-5-benzylthio-6-hydroxy-1-phenyl-10-(2-tetrahydroxypyranyloxy)-(1E,3Z)-decadiene,
(5R,6S)-5-benzylthio-6,10-dihydroxy-1-phenyl-(1E,3Z)-decadiene,
(5R,6S)-5-benzylthio-6-hydroxy-1-phenyl-10-(2-tetrahydropyranyloxy)-(1E,3E)-decadiene,
(5R,6S)-5-benzylthio-6,10-dihydroxy-1-phenyl-(1E,3E)-decadiene, and
(Z)-(3R,4S)-1-phenyl-3-phenylthio-4-hydroxy-4,8-dimethyl-nona-1,7-diene.

Throughout this specification, "R" and "S" designations are as described by Ernest L. Eliel in "Stereochemistry of Carbon Compounds", McGraw Hill (1962). The products of Example 12f and 12g are each racemic mixtures of two enantiomers and, therefore, the names given for these products are "relative" configuration names, i.e., each position identified is relative to each other. All other examples, which use the Sharpless reaction, produce a single enantiomer in view of the use of a single optical isomer of diethyl tartrate.

As seen in formula (I), at least two asymmetric carbons, i.e., those indicated by an asterisk (*), exist in the individual compounds embraced by the formula. Additional asymmetric centers could exist in view of appropriate choices for $R^4$ and $R^5$ as well as the 2-position carbon of the tetrahydropyranyl ring for $R^3$. Considering only the two carbons indicated by an asterisk (*), all invention compounds of formula (I) have opposite RS configurations. Among other materials embraced by such a definition is a racemic pair of enantiomers, one of which is in the R and S configurations, respectively, at the two asterisked carbons while the other enantiomer is in the S and R configurations, respectively, at such carbons. A second material would be a single enantiomer having either R and S or S and R configurations at the two carbon atoms designated by an asterisk.

As described hereinafter, the alkenes of formula (I) may be prepared by a ring-opening reaction on the corresponding epoxide of the following formula (II):

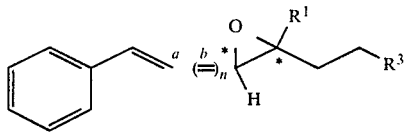

wherein
R[1] is hydrogen or methyl;
R[3] is —CH$_2$CH$_2$OH, —CH$_2$CH$_2$O(2-tetrahydropyranyl), —CH=C(CH$_3$)$_2$ or —CH(OR$^5$)$_2$
R[5] is lower alkyl;
n is 0 or 1;
a is a Z or E double bond when n is 0 and when n is 1, a is E;
b is a Z or E double bond; and
the hydrogen and R[1] moieties attached to the respective epoxy carbon atoms designated by an asterisk (*) are trans to each other.

In the epoxides of formula (II), the hydrogen and R[1] groups attached to the two carbons designated by an asterisk (*) are trans to each other, which results in their being both of either the R or S configuration. A material embraced by formula (II) could then be an R,R or S,S enantiomer or a racemate or other isomeric mixture of these two enantiomers.

Particular epoxides of formula (II) are those wherein R[3] is —CH$_2$CH$_2$O(2-tetrahydropyranyl), —CH=C(CH$_3$)$_2$ or —CH(OR$^5$); R[5] is methyl; and b is a Z double bond, with examples being:
(3S,4S)-trans-3,4-epoxy-1-phenyl-8-(2-tetrahydropyranyloxy)-1(Z)-octene,
(3S,4S)-trans-3,4-epoxy-1-phenyl-8-(2-tetrahydropyranyloxy)-1(E)octene,
(5S,6S)-1-phenyl-6,10-dimethyl-5,6-epoxy-transundeca-(1E,3Z,9)-triene,
(3S,4S)-1-phenyl-4,8-dimethyl-trans-3,4-epoxy-nonacis-1(Z)-7-diene, and
(5RS,6RS)-trans-5,6-epoxy-9,9-dimethoxy-6-methyl-1-phenylnona-(1E,3Z)-diene.

In the synthesis of compounds of the present invention, an allylic alcohol of the following formula (III) may be epoxidized to give the corresponding hydroxy compound (IVa) which is then oxidized to the aldehyde (IVb). In a Wittig reaction with a Wittig reagent having the desired structure, the epoxide (II) of the invention may be produced from aldehyde (IVb). Reaction of the epoxide (II) with the desired R$^2$SH compound yields the alkene (I) wherein p is 0, which may then be oxidized to produce the corresponding sulfinyl of formula (I) wherein p is 1:

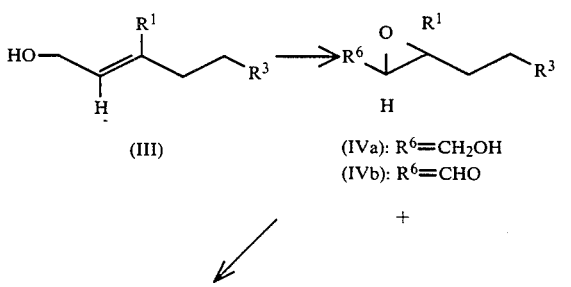

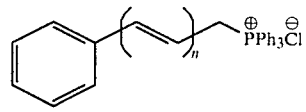

The epoxidation of the allylic alcohol (III) may be carried out by a Sharpless reaction using titanium tetraisopropoxide, (+) or (−) diethyl tartrate and tert-butyl hydroperoxide at a temperature of about −20° C. in a solvent such as methylene chloride. There is thus formed in such an asymmetric reaction, an enantiomer and the optical activity will carry through to the alkene product (I). Alternatively, the epoxide, as a diastereomeric mixture (IVa), may be produced by reaction of (III) with a peracid such as meta-chloroperbenzoic acid or perbenzoic or p-nitroperbenzoic acid or with perphthalic acid.

Oxidation of the alcohol (IVa) will then yield the corresponding aldehyde (IVb) using agents such as chromium trioxide in pyridine or pyridinium dichromate at a temperature of about 0° to 30° C., e.g. about room temperature, in an inert solvent such as methylene chloride.

Wittig reaction conditions using the aldehyde (IVb) and the phosphonium salt (V), where n is as described for formula (II) and Ph is phenyl, yields the epoxide (II). For example, the reaction may be carried out using n-butyllithium and hexamethyldisilazane or diisopropylamine in dry THF at a temperature of about −20° to −80° C., e.g. about −78° C.

Ring opening of the epoxide (II) with the appropriate R$^2$SH compound to yield (I) may be carried out in the presence of a base, e.g. an organic base such as triethylamine or pyridine in a solvent such as methanol at a temperature of about 0° to 30° C., e.g. about room temperature.

Oxidation of the alkene (I) where p is 0 to yield the corresponding alkene (I) where p is 1 may be carried out with an oxidation agent such as sodium periodate in a solvent such as methanol at about 0° to 30° C., e.g. at room temperature.

Starting materials of the formula (III) and R$^2$SH are known or may be produced by conventional techniques, e.g. a Wittig reaction.

The compounds of the invention of formulae (I) and (II) may be used as pharmaceutical agents in the treatment of inflammation and/or allergic reactions. Such activity can be exhibited by reference to the ability of the compound to inhibit the action of the enzyme 5-lipoxygenase in vitro and to reduce bronchoconstriction in vivo after ovalbumin provocation. Such testing procedures were carried out on compounds of the invention as described below:

Preparation of Cells and Cell-Free Homogenates

Rat basophilic leukemia cells (RBL-1) were grown in Eagle's Minimal Essential Medium containing 10% fetal calf serum, 5% calf serum, 1% glutamine and 50 mg/L gentamycin and were maintained at 37° C. in a atmosphere containing 5% CO$_2$. Exponentially growing cells were harvested by centrifugation at 400xg for 10 minutes at 4° C. and were washed once with Dulbecco's phosphate buffered saline containing 0.87 mM CaCl$_2$. The cells were resuspended in the same buffer at a concentration of 1.85×10$^7$ cells/ml.

5-HETE Production in Whole Cells

RBL-1 cells ($1.57 \times 10^7$ cells/tube) were preincubated for 10 minutes at 37° C. in the presence of the indicated drugs or vehicle (1% DMSO). Following the transfer of the assay tubes to an icebath, the reaction was initiated by the sequential addition of calcium ionophore A23187, an agent which increases the ability of divalent ions such as $Ca^{++}$ to cross biological membrances (final concentration=1.9 uM) and 55 uM $1-^{14}C$-arachidonic acid (New England Nuclear) at a final specific activity of 3000–4000 cpm/nmole. The final volume in each tube was 1 ml. The assay tubes were incubated at 37° C. for 5 minutes, and the reaction was stopped by transferring the tubes to ice and adjusting the pH of the reaction mixture to pH 3.0–3.5 by the addition of 1M citric acid.

Isolation and Quantitation of 5-HETE

In order to isolate the $\Delta_5$-lipoxygenase product $^{14}C$-5-HETE that was formed from arachidonic acid, each assay tube was extracted once with 6 volumes of anhydrous diethyl ether. In most assays, the recovery of product was estimated by determining the total amount of radioactivity recovered after extraction. In the remaining assays the recovery of $^{14}C$-5-HETE was monitored by addition of trace quantities of $^3H$-5-HETE (New England Nuclear) prior to extraction. The ether fractions from each sample were dried under nitrogen, redissolved and spotted on Gelman silica gel-impregnated glass fiber sheets. The plates were developed in iso-octane:2-butanone:glacial acetic acid (100:9:1). The area of each plate corresponding to added 5-HETE standard was visualized in an iodine chamber. The amount of $^{14}C$-5-HETE presented was quantitated by liquid scintillation counting in Aquasol II (New England Nuclear) and corrected for recovery. The percent inhibition of lipoxygenase activity represents the decrease in the amount of product formed from arachidonic acid by the cells or cell supernatant in the presence of drug. The values for negative controls (assays incubated on ice in the presence of citric acid) were always less than 10% of the positive controls and were subtracted from each tube. The $IC_{50}$ is the concentration of drug which is required for 50% inhibition of the enzyme, as determined graphically from assays using multiple concentrations of drug. For drugs which did not inhibit the enzyme by 50% at the highest concentration tested (10 mM), their activity is reported as having an $IC_{50}$ which is greater than 10 mM.

Active Lung Anaphylaxis

A literature reference for this test is found in the article by D. M. Ritchie et al. in Agents and Actions, Vol. 11, 396 (1981). Male Hartley guinea-pigs are actively sensitized, i.p. with 16 mg alum and 1 mg ovalbumin. Fourteen days later, these animals are anesthetized and respiration arrested by the administration of succinylcholine. Respiration is maintained at a constant pressure by a miniature Starling pump. Lung overflow changes in pressure are recorded. Animals are then pretreated with indomethacin (10 mg/kg, i.v.), atropine (0.5 mg/kg, i.v.), methysergide (0.1 mg/kg, i.v.), methapyrilene (2.0 mg/kg, i.v.) and arachidonic acid (5.0 mg/k, i.v.) prior to ovalbumin challenge. Antiallergy compounds are administered by various routes prior to ovalbumin provocation. Indications of drug efficacy are manifested as a substantial reduction in the degree of bronchoconstriction evidenced by control animals.

Bronchoconstriction induced by ovalbumin is measured as a percent of maximum bronchoconstriction (BC) obtained by clamping off the trachea. Percent inhibition of control is determined as follows:

% Inhibition of Control =

$$\frac{\text{Control \% Max } BC - \text{Treated \% Max } BC}{\text{Control \% Max } BC} \times 100$$

Pharmaceutical compositions of the invention for the treatment of inflammation or allergic reactions will comprise a pharmaceutically effective amount of an alkene (I) or an epoxide (II) or any mixtures thereof in association with a pharmaceutically acceptable diluent or carrier. For the treatment of inflammation or allergic reactions, the daily dose for a mammal, e.g. a human, will be about 1 to 500 mg per kg of body weight, preferably about 2 to 400 mg per kg, administered once or in divided doses, e.g. divided into 2–4 equal doses.

To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g. oral, inhalation or parenteral. In preparing the compositions in oral dosage form, any of the usual pharmaceutical media may be employed. Thus, for liquid oral preparation, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. For administration by inhalation, particular forms of presentation include aerosols, atomizers and vaporizers. The pharmaceutical compositions herein will contain, per dosage unit, e.g. tablet, capsule, powder, injection, teaspoonful and the like, from about 10 mg to about 1 g of the active ingredient, and, preferably, from about 50 to about 500 mg.

Also part of the present invention are the novel intermediates described herein and novel compounds of formulae (I) and (II) wherein $R^3=CH_2COOH$ and base addition salts thereof.

In the following Examples and throughout the specification, the following abbreviations may be used: mg (milligrams); g (grams); kg (kilograms); mL (milliliters); mmole or mM (millimoles); M (molar); N (normal); psi (pounds per square inch); mp (melting point); bp (boiling point); eq (equivalents); meq (milliequivalents); E (trans); Z (cis); Ph (phenyl); min (minutes); hr (hours); RT (room temperature); $Et_2O$ (diethyl ether); EtOAc (ethyl acetate); MeOH (methanol); EtOH (ethanol); LAH (lithium aluminum hydride); THF (tetrahydrofuran); DMF (dimethylformamide); p.o. (per os, orally);

EXAMPLE 1

(3R,4S)-4-Hydroxy-1-phenyl-3-phenylthio-8-(2-tetrahydropyranyloxy)-1(E)-octene a. To a solution of the aldehyde $HO(CH_2)_4CHO$, (17.98 g, 176.03 mM) in dry THF (250 mL) under $N_2$, was added the ylide $Ph_3P=CHCOOCH_3$ (61.80 g, 184.83 mM). The reaction mixture has heated to reflux for 4.5 hr, and after cooling to room temperature was concentrated in vacuo to a white slurry. Ether (500 mL) and hexane (400 mL) were added, and the mixture was cooled to 0° C. for 1 hr at which time the solids were filtered and the filtrate was concentrated in vacuo to afford the crude Wittig adduct of the formula $HO(CH_2)_4CH=CHCOOCH_3$ (38.8 g). A portion (2.0 g) was chromatographed (Silica Gel 60, 100 g) with hexane:ether (2:1) as eluent to afford pure adduct (1.38 g, 96.1%) as a clear colorless liquid.

b. To a solution of the crude adduct product of Example 1a, 70% pure by NMR (7.00 g, 30.84 mM) in $CH_2Cl_2$ (300 mL) at 0° C., under $N_2$ was added dihydropyran (4.24 mL, 46.46 mm) and a catalytic portion of para-toluenesulfonic acid monohydrate. After stirring for 20 hr, $Na_2CO_3$ (0.5 g) was added, the solids were filtered, and the reaction was concentrated in vacuo to a clear brown liquid. A solid precipitated after 16 hr. Hexane (100 mL) was added, and the solution was filtered, and concentrated in vacuo to afford crude methyl 7-(2-tetrahydropyranyloxy)-2(E)-heptenoate (9.11 g). A 2.00 g portion of the ester was chromatographed (Silica Gel 60, 200 g) with triethylamine:hexane (1:19) as eluent to afford pure methyl 7-(2-tetrahydropyranyloxy)-2(E)-heptenoate (1.34 g, 82%) as a clear colorless liquid.

c. To a solution of the crude methyl ester of Example 1b, 82% pure by NMR (5.00 g, 16.71 mM) in $CH_2Cl_2$ (125 mL) at 0° C., under $N_2$, was added diisobutylaluminum hydride (41.8 mL, 41.8 mM). After stirring for 0.5 hrs. $CH_3OH$ (5.0 mL) in $CH_2Cl_2$ followed by distilled water (2.5 mL) in $CH_3OH$ (2.5 mL) was added to the reaction mixture. After gas evolution had ceased, the mixture was filtered through a pad of celite, and concentrated in vacuo to afford crude 7-(2-tetrahydropyranyloxy)-2(E)-hepten-1-ol (3.65 g). Chromatography (Silica Gel 60, 185 g) with triethylamine, ethyl acetate:hexane (1:7:12) as eluent, afforded pure product (2.60 g, 73%) as a clear colorless liquid.

Analysis: Calculated for $C_{12}H_{22}O_3$: C, 67.25; H, 10.35. Found: C, 67.08; H, 10.40.

d. Titanium (IV) isopropoxide (13.25 mL, 44.52 mM) and (+)-diethyl L-tartrate (9.18 g 44.52 mM) were added via syringe, to methylene chloride (400 mL) kept at −20° C., under $N_2$. After 5 min, the allylic alcohol product of Example 1c (9.54 g, 44.52 mM) followed by 4.1M tert-butyl hydroperoxide (21.72 mL, 89.03 mM) were added via syringe. The reaction mixture was stirred at −20° C. for 5 hr, stoppered and stored at −10° C. for 16.5 hr. The mixture was cooled to −20° C. and 10% tartaric acid solution (100 mL) was added with vigorous stirring. The cooling bath was removed after 30 min, and stirring was continued for 1 hr. The layers were separated, and the organic solution was washed with distilled water, dried ($Na_2SO_4$), filtered and concentrated in vacuo. The residue was diluted with ether (30 mL) and cooled to 0° C. 1N NaOH (125 mL) was added and the two-phase system was stirred for 30 min. The organic layer was separated, washed with saturated NaCl solution, dried ($Na_2SO_4$), filtered, and concentrated in vacuo to afford crude (2R,3S)-7-(2-tetrahydropyranyloxy)-2,3-trans-epoxy-hepten-1-ol (8.17 g) as a clear yellow oil. Chromatography (Silica Gel 60, 700 g) with triethylamine:ethyl acetate:hexane (1:6:13) as eluent afforded pure product, (4.29 g, 42%) as a clear light-yellow oil.

Analysis: Calculated for $C_{12}H_{22}O_4$: C, 62.58; H, 9.63. Found: C, 62.43; H, 9.58.

e. Chromium trioxide (4.27 g, 42.73 mM) was added, in a single portion, to a solution of pyridine (6.91 mL, 85.44 mm) in methylene chloride. After stirring 15 min. the alcohol product of Example 1d (1.64 g, 7.12 mM) in methylene chloride (10 mL) was added via syringe. Stirring was continued for 30 min. after which time the reaction mixture was filtered through a pad of celite, and concentrated in vacuo. The dark brown residue was taken up in ether (100 mL) and filtered through the same celite pad. The filtrate was washed with saturated $CuSO_4$ solution (50 mL) and saturated NaCl solution (50 mL), dried ($Na_2SO_4$), filtered and concentrated in vacuo to afford crude (2R,3S)-7-(2-tetrahydropyranoyloxy)-2,3-trans-epoxyheptanal (1.20 g) as a clear light-yellow oil. Chromatography (Silica Gel 60, 60 g) with triethylamine:ethyl acetate:hexane (1:9:10) as eluent afforded pure product (0.95 g, 58%) as a colorless oil.

Analysis: Calculated for $C_{12}H_{20}O_4$: C, 63.13; H, 8.83. Found: C, 63.04; H, 8.78.

f. n-Butyllithium (22.92 mL, 35.75 mM) was added via syringe to a solution of hexamethyldisilazane (8.23 mL, 39.00 mM) in dry THF (350 mL) at 0° C., under $N_2$. After stirring for 15 min the phosphonium chloride $C_6H_5CH_2P+Ph_3Cl-$ (14.54 g, 37.38 mM) was added in a single portion. Stirring was continued for 30 min. at which time the aldehyde product of Example 1e (7.42 g, 32.50 mM) in dry THF (10 mL) was added via syringe. After 1 hr the reaction mixture was concentrated in vacuo, the residue was taken up in hexane:$Et_2O$ (1:1, 500 mL), filtered through a pad of celite, and concentrated in vacuo to afford a crude mixture of two epoxides (9.73 g). Chromatography (Silica Gel 60, 1000 g) with $Et_3N$:hexane (1:19 to 1:9) as eluent afforded (3S,4S)-trans-3,4-epoxy-1-phenyl-8-(2-tetrahydropyranyloxy)-1(Z)-octene (5.16 g, 52%) as a clear colorless oil.

Analysis: Calculated for $C_{19}H_{26}O_3$: C, 75.46; H, 8.67. Found: C, 75.38; H, 8.61.

Further elution afforded (3S,4S)-trans-3,4-epoxy-1-phenyl-8-(2-tetrahydropyranyloxy)-1(E)-octene (2.84 g, 29%) as a clear colorless oil.

Analysis: Calculated for $C_{19}H_{26}O_3$: C, 75.46; H, 8.67. Found: C, 75.51; H, 8.77.

g. Thiophenol (2.34 mL, 22.82 mM), $CH_3OH$ (75 mL), and triethylamine (6.36 mL, 45.63 mM), were added sequentially to the (E) epoxide product of Example 1f (2.30 g, 7.61 mM) under $N_2$. After stirring overnight the reaction mixture was concentrated in vacuo to afford crude (3R,4S)4-hydroxy-1-phenyl-3-phenylthio-8-(2-tetrahydropyranyloxy)-1(E)-octene (4.69 g) as a clear yellow oil. Chromatography (Silica Gel 60, 70–230 mesh, 500 g) with $Et_3N$:EtOAc:Hexane (1:2:17 to 1:4:15) as eluent afforded pure product (3.13 g, 99.7%) as a clear light-yellow oil.

Analysis: Calculated for C$_{25}$H$_{32}$O$_3$S: C, 72.77; H, 7.82. Found: C, 72.55; H, 7.84.

EXAMPLE 2

(5R,6S)5-(4-Chlorophenylthio)-6,10-dimethyl-6-hydroxy-1-phenylundeca-(1E,3Z,9)-triene.¼Hydrate a. To a cooled (−20° C.) solution of Ti(iOPr)$_4$ (23.7 mL, 80 mM) in dichloromethane (600 mL) was added sequentially (+)-diethyl tartrate (15.0 mL, 88 mM), and geraniol (12.3 mL, 80 mM). The resulting mixture was stirred 5 min at −20° C. and a 1,2-dichloroethane solution of anhydrous tert-butylhydroperoxide (40 mL, 4.0M, 160 mM, 2eq) was added. The resulting homogeneous mixture was kept at −10° C. overnight. The mixture was cooled to −20° C. and a 10% tartaric acid solution (200 mL) was added. The −20° C. temperature was maintained for 0.5 hr after which time the solution was allowed to warm to ambient temperature for 1 hr. The dichloromethane layer was separated, and the aqueous layer was extracted once with dichloromethane (100 mL). The combined dichloromethane solutions were washed once with water (200 mL) and 10% sodium sulfite (200 mL), and suction filtered through a pad of celite. The filtrate was concentrated in vacuo to an oil, which was taken up in ether (500 mL), cooled to 0° C., and treated with 1N NaOH (240 mL) for 0.5 hr. The ether layer was washed once with saturated NaCl solution (200 mL), dried over anhydrous Na$_2$SO$_4$, and suction filtered through a pad of celite. The filtrate was concentrated in vacuo to an oil (14 g) which was chromatographed on silica gel 60, 70–230 mesh (300 g). The product (2S,3S)-3,7-dimethyl-1-hydroxy-trans-2,3-epoxyoct-6-ene (7.35 g, 54%) was eluted with hexane:ethyl acetate (7:3).

b. To the epoxy alcohol product of Example 2a (6.35 g, 37.3 mM) in dichloromethane (400 mL) was added pyridinium dichromate (40.0 g, 115 mM, 3eq) in a single portion. The reaction mixture was stirred overnight at RT and suction filtered through a pad of celite. The filtrate was concentrated in vacuo, taken up in ether (100 mL), and suction filtered through a pad of celite. The filtrate was concentrated to a light yellow oil (6.8 g), which was chromatographed on silica gel 60, 70–230 mesh (300 g) and eluted with hexane:ethyl acetate (7:3) to yield (2R,3S)-trans-2,3-epoxy-3,7-dimethyloct-6-en-al.⅜H$_2$O (3.00 g, 48%).

Analysis: Calculated for C$_{10}$H$_{16}$O$_2$.⅜H$_2$O: C, 66.64; H, 9.69. Found: C, 66.53; H, 9.94.

c. A solution of diisopropylamine (3.36 mL, 24.0 mM) in THF (100 mL) at 0° C. was treated with n-BuLi (14.1 mL, 1.56M, 22.0 mM). After 15 min the phosphonium salt C$_6$H$_5$CH=CHCH$_2$P+Ph$_3$Cl− (8.40 g, 22 mM) was added in a single portion. After 10 min the red-orange solution of the ylide was cooled to −70° C. and the aldehyde product of Example 2b (3.36 g, 20.0 mM) dissolved in THF (10 mL) was added. The reaction mixture was maintained at −70° C. for 0.5 hr and then warmed to 0° C. over 1.5 hr. Hexane (150 mL) was added, and the mixture was suction filtered through a pad of celite. The filtrate was concentrated in vacuo and the residue was treated with hexane:Et$_3$N (9:1) (100 mL). The material was again filtered and concentrated in vacuo to an orange liquid (5.36 g). The crude product was purified by column chromatography on Silica Gel 60 (70–230 mesh) (300 g) and eluted with hexane:Et$_3$N (9:1) to afford the epoxide (5S,6S)1-phenyl-6,10-dimethyl-5,6-epoxy-trans-undeca-(1E,3Z,9)-triene.1/10hydrate (4.40 g, 82%) [α]$_D^{26}$(CHCl$_3$)+105.7°.

Analysis: Calculated for C$_{19}$H$_{24}$O.1/10H$_2$O: C, 84.46; H, 9.03. Found: C, 84.24; H, 8.82.

d. The epoxide product of Example 1c (1.34 g, 5.0 mmol) was dissolved in methanol (50 mL) containing triethylamine (4.0 mL), p-Chlorothiophenol (1.45 g, 10 mmol) was added, and the mixture was stirred overnight at room temperature. The reaction mixture was concentrated in vacuo to afford a vacous orange oil (3.6 g). Purification by column chromatography [Silica Gel 60; 70–230 mesh (230 g)] and elution with hexane:Et$_2$O (9:1) afforded (5R,6S)5-(4-chlorophenylthio)-6,10-dimethyl-6-hydroxy-1-phenylundeca-(1E,3Z,9)-triene.¼hydrate (1.25 g, 61%).

Analysis: Calculated for C$_{25}$H$_{29}$ClOS.¼H$_2$O: C, 71.91; H, 7.12. Found: C, 71.97; H, 7.14.

EXAMPLE 3

Methyl N-Acetyl-S-3-[(3R,4S)-4-hydroxy-1-phenyl-8-(2-tetrahydroxypyranyloxy)-1(Z)-octenyl](R)cysteinate a. N-Acetyl-L-cysteine (5 g, 30.6 mM) was treated with excess diazomethane (generated from N-nitrosomethyl urea) in ether for 6 hr at RT. Unreacted starting material was removed by filtration and the resulting yellow filtrate was allowed to stand overnight. The solvent was removed in vacuo and the residue crystallized from Et$_2$O/Pet. ether to give pure N-acetyl-L-cysteine methyl ester (650 mg); mp 73°–76° C. compared to a literature mp of 81°–82° C. in the Journal of Organic Chemistry, Vol. 35, p. 3542 (1970) and 79°–80° C. in the Canadian Journal of Chemistry, Vol. 44, p. 2517 (1966).

b. N-Acetyl cysteine methyl ester made as described in Example 3a (1.74 g, 9.82 mM), CH$_3$OH (30 mL) and triethylamine (2.72 mL, 19.64 mM), were added sequentially to the (Z) epoxide product of Example 1f (0.99 g, 3.27 mM) under N$_2$. After stirring overnight, the reaction mixture was concentrated in vacuo to afford crude methyl N-acetyl-S-3-[(3R,4S)-4-hydroxy-1-phenyl-8-(2-tetrahydroxypyranyloxy)-1(Z)-octenyl](R) cysteinate (2.79 g) as a clear yellow oil.

EXAMPLE 4

Methyl N-Acetyl-S-3-[(3R,4S)-4,8-dihydroxy-1-phenyl-1(Z)-octenyl](R)-cysteinate.¼Hydrate The crude product of Example 3 was diluted with CH$_3$OH (30 mL) and a catalytic amount of p-toluenesulfonic acid was added. After 3 hr the reaction mixture was neutralized and dried with Na$_2$CO$_3$, filtered and concentrated in vacuo. The remaining residue was taken up in CH$_2$Cl$_2$, filtered and concentrated in vacuo to afford crude product (1.25 g). Chromatography (Silica Gel 60, 70–230 mesh, 125 g) with CH$_3$OH:CH$_2$Cl$_2$ (1:19) as eluent afforded methyl N-acetyl-S-3-[(3R,4S)-4,8-dihydroxy-1-phenyl-1(Z)-octenyl](R)-cysteinate.¼hydrate (0.85 g, 66%) as a clear colorless oil.

Analysis: Calculated for C$_{20}$H$_{29}$NO$_5$S.¼H$_2$O: C, 60.05; H, 7.43; N, 3.50. Found: C, 60.02; H, 7.52; N, 3.46.

EXAMPLE 5

(3R,4S) 1-Phenyl-3-phenylthio-1-(E)-octen-4,8-diol

A catalytic amount of p-toluenesulfonic acid was added to a solution of the THP-ether product of Example 1g (1.22 g, 2.96 mM) in CH$_3$OH (30 mL). After stirring overnight the reaction mixture was neutralized and dried with Na$_2$CO$_3$, filtered and concentrated in vacuo. The residue was taken up in CH$_2$Cl$_2$, filtered and concentrated in vacuo to afford crude product (1.10 g), as a clear light brown oil. Chromatography (Silica Gel 60, 230–400 mesh, 40 g) with CH$_3$OH:CH$_2$Cl$_2$ (1:39) as eluent, afforded the title compound (0.89 g, 91%) as a clear colorless oil, which was recrystallized from hexane:ether to a white crystalline solid, mp=65°–66° C.

Analysis: Calculated for C$_{20}$H$_{24}$O$_2$S: C, 73.13; H, 7.36. Found: C, 73.04; H, 7.42.

EXAMPLE 6

Methyl N-Acetyl-S-3[(5R,6S)-1-phenyl-6-hydroxy-6,10-dimethylundeca-(1E,3Z,9)-trienyl]-(R)-cysteinate The epoxide product of Example 2c (1.34 g, 5.0 mM) was dissolved in anhydrous CH$_3$OH (50 mL) and treated successively with triethylamine (4.0 mL, 30 mM) and N-acetylcysteine methyl ester (2.66 g, 15 mM). The mixture was degassed and stirred overnight at RT. The solution was concentrated in vacuo and chromatographed [Silica Gel 60 (70–230 mesh), 300 g]. Elution with Et$_2$O:EtOAc (1:1) afforded the title product (1.28 g, 57%) as a viscous oil $[\alpha]_D^{23}$ (CHCl$_3$)+285°.

Analysis: Calculated for C$_{25}$H$_{35}$NO$_4$S: C, 67.38; H, 7.92; N, 3.14. Found: C, 66.92; H, 7.95; N, 3.10.

EXAMPLE 7

(5R,6S) 1-Phenyl-5-phenylthio-6-hydroxy-6,10-dimethylundeca-(1E,3Z,9)-triene Monohydrate The epoxide product of Example 2c (0.95 g, 3.54 mM) was dissolved in anhydrous CH$_3$OH and treated successively with triethylamine (2.95 mL, 21.2 mM) and thiophenol (1.09 mL, 10.6 mM). The reaction mixture was degassed and stirred overnight at RT. The solution was concentrated in vacuo and the residue was chromatographed [Silica Gel 60 (70–230 mesh) 150 g]. Elution with hexanes:Et$_3$N (9:1) afforded the title product 1.20 g, 90%) as a very light-yellow viscous oil $[\alpha]_D^{26}$ (CHCl$_3$)+340.2°.

Analysis: Calculated for C$_{25}$H$_{30}$OS.H$_2$O: C, 75.71; H, 8.13. Found: C, 75.98; H, 7.93.

EXAMPLE 8

(3R,4S) 4-Hydroxy-1-phenyl-3-phenylthio-8-(2-tetrahydropyranyloxy)-1(Z)-octene

Thiophenol (3.96 mL, 38.59 mM), CH$_3$OH (125 mL), and triethylamine (10.76 mL, 77.18 mM) were added sequentially to the (Z) epoxide product of Example 1f (3.89 g, 12.86 mM) under N$_2$. After stirring overnight, the reaction mixture was concentrated in vacuo to afford crude product (6.89 g) as a clear yellow oil. Chromatography (Silica Gel 60, 70–230 mesh, 700 g) with Et$_3$N:EtOAc:hexane (1:2:17 to 1:4:15) as eluent afforded the title compound (5.06 g, 95%) as a clear colorless oil.

Analysis: Calculated for C$_{25}$H$_{32}$O$_3$S: C, 72.77; H, 7.82. Found: C, 72.50; H, 7.93.

EXAMPLE 9

(3R,4S) 1-Phenyl-3-phenylthio-1(Z)-octen-4,8-diol

A catalytic amount of p-toluenesulfonic acid was added to a solution of the THP-ether product of Example 8 (1.24 g, 3.01 mM) in CH$_3$OH (30 mL). After stirring overnight, the reaction mixture was neutralized and dried with Na$_2$CO$_3$, filtered, and concentrated in vacuo. The remaining residue was taken up in CH$_2$Cl$_2$, filtered and concentrated in vacuo to afford crude product (1.04 g) as a clear light-yellow oil. Chromatography (Silica Gel 60, 230–400 mesh, 40 g) with CH$_3$OH:CH$_2$Cl$_2$ (1:39) as eluent afforded the title product (0.84 g, 85%) as a clear colorless oil.

Analysis: Calculated for C$_{20}$H$_{24}$O$_2$S: C, 73.13; H, 7.36. Found: C, 73.64; H, 7.43.

EXAMPLE 10

(3R,4S) 4-Hydroxy-1-phenyl-3-phenylsulfinyl-8-(2-tetrahydropyranyloxy)-1(E)-octene Powdered sodium periodate (0.82 g, 3.84 mM) was added to a solution of the sulfide product of Example 1g (1.44 g, 3.49 mM) in CH$_3$OH (35 mL). H$_2$O was added to the reaction mixture until the sulfide began to precipitate. The reaction was stirred overnight and concentrated in vacuo, and the residue was dissolved in CH$_2$Cl$_2$ (100 mL). The CH$_2$Cl$_2$ solution was washed with H$_2$O (15 mL), dried (Na$_2$SO$_4$), filtered and concentrated in vacuo to afford crude product (1.68 g) as a clear light-yellow oil. Chromatography (Silica Gel 60, 230–400 mesh, 70 g) with Et$_3$N:EtOAc:hexane (1:4:15 to 1:10:9) as eluent afforded pure title product (0.95 g, 63%) as a white crystalline solid mp=98°–99° C.

Analysis: Calculated for C$_{25}$H$_{32}$O$_4$S: C, 70.06; H, 7.53. Found: C, 69.87; H, 7.54.

EXAMPLE 11

Methyl N-Acetyl-S-3-[(3R,4S)-1-phenyl-4-hydroxy-4,8-dimethylnona-1(Z)-7-dienyl]-(R)-cysteinate.⅓H$_2$O a. Diisopropylamine (0.56 mL, 4.0 mM) was dissolved in THF (30 mL) and treated at RT with n-BuLi (1.54 mL, 2.46M, 3.8 mM). The phosphonium salt (C$_6$H$_3$CH$_2$P+Ph$_3$Cl−, 1.56 g, 4.0 mM) was added and after 5 min, the mixture was cooled to −78° C. and the epoxide product of Example 2b (0.58 g, 3.45 mM) was added in THF (7 mL). The reaction mixture was maintained at −78° C. for 0.5 hr then quickly suction-filtered through a pad of celite, and concentrated in vacuo. The residue was taken up in hexanes (50 mL) and the product was separated from most of the triphenylphosphine oxide by filtration and washing with hexanes. The filtrate was concentrated and the residue was chromatographed on silica gel 60, 70–230 mesh (80 g). The product was eluted with hexanes:Et$_2$O:Et$_3$N (20:10:3) to yield 1-phenyl-4,8-dimethyl-trans-3,4-epoxy-nona-cis-1,7-diene (0.65 g, 78%) as a nearly colorless oil $[\alpha]_D^{24}$ (CHCl$_3$)−72.3°.

Analysis: Calculated for C$_{17}$H$_{22}$O.1/10H$_2$O: C, 83.62; H, 9.16. Found: C, 83.55; H, 9.40.

b. N-Acetyl cysteine methyl ester (1.59 g, 9.0 mM, 3 eq) was dissolved in a mixture of CH$_3$OH (30 mL) and triethylamine (2.5 mL, 18 mM, 6 eq). To this solution was added the epoxide product of Example 11a (0.73 g, 3.0 mM) in a minimum amount of CH$_3$OH. The resulting mixture was degassed and left at RT overnight. The crude reaction mixture was concentrated in vacuo and chromatographed on silica gel 60, 70–230 mesh (250 g). The product methyl N-acetyl-S-3-[(3R,4S)-1-phenyl-4-hydroxy-4,8-dimethyl-nona-1(Z)-7-dienyl]-(R)-cysteinate.½H$_2$O (1.00 g, 79%) was eluted with ethyl acetate [α]$_D^{24}$ (CHCl$_3$)+97.5°.

Analysis: Calculated for C$_{23}$H$_{33}$NO$_4$S.½H$_2$O: C, 64.91; H, 7.98. Found: C, 64.80; H, 7.82.

EXAMPLE 12

(5RS,6SR) 9,9-Dimethoxy-6-hydroxy-6-methyl-1-phenyl-5-phenylthio-(1E,3Z)-nonadiene a. Geranyl acetate (48 g, 0.24 mol) was ozonized with O$_3$ in EtOAc (1 liter) at −60° C. The mixture stood overnight, and was then quenched with dimethyl sulfide (10 mL) and concentrated to 58.9 g of CH$_3$C(O)OCH$_2$CH=C(CH$_3$)CH$_2$CH$_2$CHO.

b. The crude product of Example 12a in benzene (200 mL) was treated with (MeO)$_3$CH (60 mL, 0.55 mol) and catalytic p-toluenesulfonic acid. The mixture stood overnight at room temperature, after which time it was quenched with a small quantity of K$_2$CO$_3$ and filtered. Concentration afforded 67.2 g of crude CH$_3$(O)OCH$_2$CH=C(CH$_3$)CH$_2$CH$_2$CH(OCH$_3$)$_2$.

c. The crude product of Example 12b was treated with K$_2$CO$_3$ (35 g, 0.25 mol) in MeOH (300 mL) at 0°. The mixture was concentrated after 4 hr, taken up in Et$_2$O, filtered and concentrated to give 30.6 g of crude HOCH$_2$CH=C(CH$_3$)CH$_2$CH$_2$CH(OCH$_3$)$_2$. The crude product was chromatographed on Silica Gel 60 (1 kg; 70–230 mesh) and was eluted with Hex:Et$_2$O:Et$_3$N (50:50:1) to afford recovered geraniol (9.6 g), and pure product (12.88 g) 30%; 40% yield based on recovered geraniol.

d. The acetal product of Example 12c (4.40 g, 25.2 mmol) in CH$_2$Cl$_2$ (100 mL) at 0° C. was combined with meta-chloroperbenzoic acid (5.0 g, 29 mmol) and the mixture was warmed to RT and stirred overnight. Ca(OH)$_2$ (2.2 g, 30 mmol) was added, the mixture was stirred 0.5 hr and then filtered through a pad of celite. The filtrate was concentrated, taken up in Et$_2$O and filtered again. Concentration of the filtrate afforded 5.0 g of the epoxide HOCH$_2$CH(O)C(CH$_3$)CH$_2$CH$_2$CH(OCH$_3$)$_2$.

e. The crude epoxide product of Example 12d in CH$_2$Cl$_2$ (20 mL) was added to CrO$_3$ pyridine prepared from 18.0 g CrO$_3$ (150 mmol, 6 eq) and 24.2 mL pyridine (300 mmol, 12 eq) in CH$_2$Cl$_2$ (300 mL) at 0° for 15 min. After 40 min the mixture was filtered through a pad of celite, the filtrate was concentrated, taken up in Et$_2$O (200 mL) and filtered again. The ether solution was washed with CuSO$_4$ (100 mL), dried over Na$_2$SO$_4$, filtered and concentrated to afford the aldehyde epoxide HOCCH(O)C(CH$_3$)CH$_2$CH$_2$CH(OCH$_3$)$_2$, 2.15 g.

f. To a solution of LDA formed from n-BuLi (12.2 mmol) and diisopropylamine (1.95 mL, 14 mmol) in THF (125 mL) at 0° was added the phosphonium salt (C$_6$H$_5$CH=CH—CH$_2$P+Ph$_3$Cl−) neat (5.88 g, 14 mmol). After 5 min at 0° the red ylide was treated with the epoxyaldehyde product of Example 12e (2.10 g, 11.1 mmol) in THF (15 mL). The mixture was kept at 0° for 1 hr, after which time hexane (200 mL) was added and the mixture filtered. The filtrate was concentrated, again taken up in hexane (100 mL) and filtered. Concentration provided 3.2 g of crude oil; chromatography on Silica Gel 60, 70–230 mesh (600 g), and elution with Hexane:Et$_3$N (19:1) gave (5RS,6RS) trans-5,6-epoxy-9,9-dimethoxy-6-methyl-1-phenylnona-(1E,3Z)-diene.¼ H$_2$O, 1.47 g (46%) as a light yellow oil, as well as the trans, trans isomer (0.46 g, 14%) and a mixture of the two compounds (0.17 g, 4%) as light yellow oils.

Analysis: Calculated for C$_{18}$H$_{24}$O$_3$.¼H$_2$O: C, 73.81; H, 8.43. Found: C, 74.12; H, 8.18.

g. The dimethylacetal product of Example 12f (0.90 g, 3.12 mmol) in CH$_3$OH (30 mL) and triethylamine (2.5 mL, 18 mmol) was treated with thiophenol (0.35 mL, 3.43 mmol) at room temperature. The mixture was stirred overnight at room temperature and concentrated to an oil (1.36 g). Purification by column chromatography with Silica Gel 60, 70–230 mesh (125 g) and elution with Et$_2$O:Hexane:Et$_3$N (1:1:0.01) afforded 1.02 g (82%) of (5RS,6SR) 9,9-dimethoxy-6-hydroxy-6-methyl-1-phenyl-5-phenylthio-(1E,3Z)-nonadiene after crystallization from Et$_2$O, mp 59.5°–61°.

Analysis: Calculated for C$_{24}$H$_{30}$O$_3$S: C, 72.32; H, 7.59. Found: C, 72.20; H, 7.76.

EXAMPLE 13

(5R,6S)-5-Benzylthio-6-hydroxy-1-phenyl-10-(2-tetrahydropyranyloxy)-(1E,3Z)-decadiene a. n-Butyllithium (16.35 mL, 36.80 mM) was added via syringe to a 1-liter round bottom flask containing a solution of hexamethyldisilazane (8.50 mL, 40.30 mM) in dry THF (400 mL) at 0° C., under N$_2$. After stirring for 15 min. the phosphonium chloride C$_6$H$_5$CH=CHCH$_2$P+—Ph$_3$Cl− (15.99 g, 38.55 mM) was added in a single portion. Stirring was continued for 15 min. at which time the aldehyde product of Example 1e (8.00 g, 35.04 mM) diluted with dry THF (10 mL) was added via an addition funnel, keeping the reaction temperature below 5° C. After 30 min the reaction mixture was concentrated in vacuo and the residue was dissolved in Et$_2$O:hexane (3:1, 1000 mL), filtered through a pad of celite, and concentrated in vacuo to afford a crude mixture of the 1(E), 3(Z) and 1(E), 3(E) decadiene epoxides (12.63 g). Chromatography (Baker 40 νm silica gel, 500 g) with Et$_3$N:hexane (1:19) as eluent afforded (5S,6S)-trans-5,6-epoxy-1-phenyl-10-(2-tetrahydropyranyloxy)-(1E,3Z)-decadiene (2.14 g), (5S,6S)-trans-5,6-epoxy-1-phenyl-10-(2-tetrahydropyranyloxy)-(1E,3E)-decadiene (0.99 g) and a mixture of the two (2.14 g). The mixture was rechromatographed (Baker 40 μm silica gel, 107 g) with Et$_3$N:hexane (1:19) as eluent to afford a total yield of the (1E,3Z) isomer (2.93 g, 25%) and the (1E,3E) isomer (2.19 g, 19%) as clear yellow oils.

b. Triethylamine (2.13 mL, 15.25 mM) followed by CH$_3$OH (60 mL) were added to a 200 mL round bottom flask containing the (1E,3Z) epoxide product of Example 13a (1.67 g, 5.08 mM). This mixture was degassed and placed under N$_2$. Benzylmercaptan (0.90 mL, 7.63 mM) was added via syringe and the reaction mixture was again degassed and placed under N$_2$. After stirring overnight at room temperature, the reaction mixture was concentrated in vacuo to afford crude product (2.61 g). Chromatography (Baker 40 μm silica gel, 78 g) with Et$_3$N:EtOAc:hexane (1:5:14) as eluent afforded (5R,6S)-5-benzylthio-6-hydroxy-1-phenyl-10-(2-tetrahydropyranyloxy)-(1E,3Z)-decadiene (2.20 g, 96%) as a clear light-yellow oil.

EXAMPLE 14

(5R,6S)-5-Benzylthio-6,10-dihydroxy-1-phenyl-(1E,3Z)-decadiene

A catalytic amount of p-toluenesulfonic acid was added to a 500 mL round bottom flask containing the THP-ether product of Example 13b (2.12 g, 4.68 mM) in CH₃OH (50 mL). After stirring for 3 hr at room temperature, the reaction mixture was neutralized with Na₂CO₃, filtered through a celite pad, and concentrated in vacuo. The residue was taken up in CH₂Cl₂ (100 mL), filtered through a pad of celite, and concentrated in vacuo to afford (5R,6S)-5-benzylthio-6,10-dihydroxy-1-phenyl-(1E,3Z)-decadiene (1.69 g, 98%) as a light-yellow oil.

EXAMPLE 15

Sodium (5R-6S)-5-Benzylthio-6-hydroxy-1-phenyl-(1E,3Z)-decadienoate Hydrate a. Benzene (250 mL) was added to a 1-liter round bottom flask protected from light, containing Fetizon's reagent (Ag₂CO₃ on celite, 44.3 g, 65.53 mM in Ag₂CO₃). This mixture was heated to remove residual H₂O by azeotropic distillation with benzene. The diol product of Example 14 (1.61 g, 4.37 mM) in benzene (10 mL) was added to the reaction mixture. After stirring at reflux for 19 hr, the reaction mixture was allowed to cool to room temperature, at which time it was filtered through a celite pad. The filter cake was washed with benzene (150 mL), and the benzene solutions were combined and concentrated in vacuo to afford crude lactone (1.30 g). Chromatography (Baker 40 μm silica gel, 52 g) with EtOAc:Hexane (3:7) as eluent afforded the lactone (0.61 g, 38%) as a clear yellow oil.

b. 1N NaOH (1.48 mL, 1.48 mM) was added to a 250 mL round bottom flask containing the lactone product of Example 15a (0.54 g, 1.48 mM) in CH₃OH (10 mL). After stirring for 2 days, H₂O (50 mL) was added to the reaction mixture and the CH₃OH was removed in vacuo. The remaining aqueous solution was washed with Et₂O (15 mL), and any remaining Et₂O or CH₃OH was removed in vacuo at 40° C. The aqueous solution was lyophilized to afford crude sodium (5R,6S)-5-benzylthio-6-hydroxy-1-phenyl-1(E),3(Z)-decadienoate hydrate (0.52 g). The crude product was dissolved in H₂O (50 mL), acidified with 3N HCl, and extracted with CH₂Cl₂. The CH₂Cl₂ solution was dried (Na₂SO₄), filtered through a pad of celite, and concentrated in vacuo to afford the free acid (0.43 g). The free acid was dissolved in CH₃OH (10 mL), and 1N NaOH (1.12 mL, 1.12 mM) was added. The reaction mixture was heated to reflux for 4 hr, at which time the CH₃OH was removed on the rotovap. The residue was diluted with H₂O (60 mL) and washed with Et₂O (25 mL). The last traces of CH₃OH and Et₂O were removed in vacuo at 40° C., and the aqueous solution was lyophilized to afford the title compound (0.44 g, 70%) as a tan solid mp=136.5°–139.0° C.

Analysis: Calculated for C₂₃H₂₅NaO₃S•H₂O: C, 65.38; H, 6.44. Found: C, 65.46; H, 6.17.

EXAMPLE 16

(5R,6S)-5-Benzylthio-6-hydroxy-1-phenyl-10-(2-tetrahydropyranyloxy)-(1E,3E)-decadiene In a manner similar to the procedure of Example 13, the (1E,3E) epoxide produced in Example 13a (2.11 g, 6.42 mM) was converted to the title product (2.64 g, 91%).

EXAMPLE 17

(5R,6S)-5-Benzylthio-6,10-dihydroxy-1-phenyl-(1E,3E)-decadiene

In a manner similar to the procedure of Example 14, the product of Example 16 (2.61 g 5.77 mM) was converted to the title product (2.12 g, 99.7%).

EXAMPLE 18

Sodium (5R,6S)-5-Benzylthio-6-hydroxy-1-phenyl-(1E,3E)-decadienoate Sesquihyrate In a manner similar to the procedure of Example 15, the product of Example 17 (2.05 g, 5.56 mM) was converted to the lactone (0.67 g, 33%) and then to the title product (0.50 g, 67%), mp=140°–143° C.

Analysis: Calculated for C₂₃H₂₅NaO₃S.1½H₂O: C, 64.01; H, 6.54. Found: C, 63.92; H, 6.20.

EXAMPLE 19

(3R,4S)-1-Phenyl-3-phenylthio-4-hydroxy-4,8-dimethylnona-1(Z),7-diene Monohydrate The epoxide product of Example 11a (0.73 g, 3.0 mM) was dissolved in a solution of CH₃OH (30 mL) which contained triethylamine (2.5 mL, 18 mM, 6 eq). Thiophenol (0.92 mL, 9.0 mM, 3 eq) was added and the resulting colorless solution was kept at RT overnight. The mixture was concentrated in vacuo, and the residue was chromatographed on silica gel 60, 70–230 mesh (150 g). The title product (0.78 g, 74%) eluted with hexanes:Et₂O:Et₃N (20:10:3) as a nearly colorless oil [α]$_D^{24}$(CHCl₃) +248.8°.

Analysis: Calculated for C₂₃H₂₈OS.1 H₂O: C, 74.55; H, 7.62. Found: C, 74.41; H, 7.99.

What is claimed is:

1. An alkene of the following formula (I):

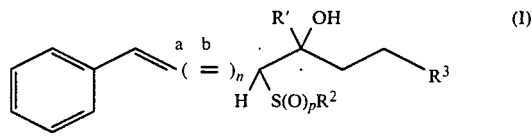

wherein
R¹ is hydrogen or methyl;
R² is phenyl, halogen-substituted phenyl, benzyl or —CH₂CH(COOR⁴)NHR⁷;
R³ is —CH₂CH₂OH, —CH₂CH₂O(2-tetrahydropyranyl), —CH=C(CH₃)₂ or —CH(OR⁵)₂
R⁴ is lower alkyl;
R⁵ is lower alkyl;
R⁷ is lower alkanoyl;
n is 0 or 1;
a is a Z or E double bond when n is 0 and when n is 1, a is a E double bond;
b is a Z or E double bond;
p is 0 or 1; and
the two carbon atoms designated by an asterisk (*) are of the opposite RS configurations.

2. The alkene of claim 1, wherein said alkene is a racemic pair of enantiomers, one of which is in the R and S configurations, respectively, at the two asterisked carbons while the other enantiomer is in the S and R configurations, respectively, at such carbons.

3. The alkene of claim 1, wherein said alkene is an enantiomer having either R and S or S and R configurations at the two carbon atoms designated by an asterisk.

4. The alkene of claim 1, wherein said halogen-substituted phenyl is phenyl substituted by a single fluoro, chloro, bromo or iodo; said lower alkyl is alkyl of 1 to 4 carbons; and said lower alkanoyl is alkanoyl of 2 to 4 carbons.

5. The alkene of claim 1, wherein p is 0.

6. The alkene of claim 1, wherein $R^2$ is phenyl; $R^3$ is —CH$_2$CH$_2$O(2-tetrahydropyranyl) or —CH=C(CH$_3$)$_2$; n is 0; and p is 0.

7. The alkene of claim 1, wherein said alkene is selected from the group consisting of:
(3R,4S)-4-hydroxy-1-phenyl-3-phenylthio-8-(2-tetrahydropyranyloxy)-1(E)-octene.
(5R,6S)-5-(4-chlorophenylthio)-6,10-dimethyl-6-hydroxy-1-phenylundeca-(1E,3Z,9)-triene,
methyl N-acetyl-S-3-[(3R,4S)-4-hydroxy-1-phenyl-8-(2-tetrahydropyranyloxy)-1(Z)-octenyl]-(R)-cysteinate,
methyl N-acetyl-S-3-[(3R,4S)-4,8-dihydroxy-1-phenyl-1(Z)-octenyl]-(R)-cysteinate,
(3R,4S)-1-phenyl-3-phenylthio-1(E)-octen-4,8-diol,
methyl N-acetyl-S-3-[(5R,6S)-1-phenyl-6-hydroxy-6,10-dimethylundeca-(1E,3Z,9)-trienyl]-(R)-cysteinate,
(5R,6S)-1-phenyl-5-phenylthio-6-hydroxy-6,10-dimethylundeca-(1E,3Z,9)-triene,
(3R,4S)-4-hydroxy-1-phenyl-3-phenylthio-8-(2-tetrahydropyranyloxy)-1(Z)-octene,
(3R,4S)-1-phenyl-3-phenylthio-1(Z)-octen-4,8-diol,
(3R,4S)-4-hydroxy-1-phenyl-3-phenylsulfinyl-8-(2-tetrahydropyranyloxy)-1(E)-octene,
methyl N-acetyl-S-3-[(3R,4S)-1-phenyl-4-hydroxy-4,8-dimethylnona-1(Z)-7-dienyl]-(R)-cysteinate,
(5RS,6SR)-9,9-dimethoxy-6-hydroxy-6-methyl-1-phenyl-5-phenylthio-(1E,3Z)-nonadiene,
(5R,6S)-5-benzylthio-6-hydroxy-1-phenyl-10-(2-tetrahydropyranyloxy)-(1E,3Z)-decadiene
(5R,6S)-5-benzylthio-6,10-dihydroxy-1-phenyl-(1E,3Z)-decadiene,
(5R,6S)-5-benzylthio-6-hydroxy-1-phenyl-10-(2-tetrahydroxypyranyloxy)-(1E,3E)-decadiene,
(5R,6S)-5-benzylthio-6,10-dihydroxy-1-phenyl-(1E,3E)-decadiene, and
(3R,4S)-1-phenyl-3-phenylthio-4-hydroxy-4,8-dimethyl-nona-1(Z),7-diene. -

8. The alkene of claim 1, wherein said alkene is (3R,4S)-4-hydroxy-1-phenyl-3-phenylthio-8-(2-tetrahydropyranyloxy)-1(E)-octene.

9. The alkene of claim 1, wherein said alkene is (5R,6S)-5-(4-chlorophenylthio)-6,10-dimethyl-6-hydroxy-1-phenylundeca-(1E,3Z,9)-triene.

10. The alkene of claim 1, wherein said alkene is methyl N-acetyl-S-3-[(3R,4S)-4-hydroxy-1-phenyl-8-(2-tetrahydropyranyloxy)-1(Z)-octenyl]-(R)-cysteinate.

11. The alkene of claim 1, wherein said alkene is methyl N-acetyl-S-3-[(3R,4S)-4,8-dihydroxy-1-phenyl-1(Z)-octenyl]-(R)-cysteinate.

12. The alkene of claim 1, wherein said alkene is (3R,4S)-1-phenyl-3-phenylthio-1(E)-octen-4,8-diol.

13. The alkene of claim 1, wherein said alkene is methyl N-acetyl-S-3-[(5R,6S)-1-phenyl-6-hydroxy-6,10-dimethylundeca-(1E,3Z,9)-trienyl]-(R)-cysteinate.

14. The alkene of claim 1, wherein said alkene is (5R,6S)-1-phenyl-5-phenylthio-6-hydroxy-6,10-dimethylundeca-(1E,3Z,9)-triene.

15. The alkene of claim 1, wherein said alkene is (3R,4S)-4-hydroxy-1-phenyl-3-phenylthio-8-(2-tetrahydropyranyloxy)-1(Z)-octene.

16. The alkene of claim 1, wherein said alkene is (3R,4S)-1-phenyl-3-phenylthio-1(Z)-octen-4,8-diol.

17. The alkene of claim 1, wherein said alkene is (3R,4S)-4-hydroxy-1-phenyl-3-phenylsulfinyl-8-(2-tetrahydropyranyloxy)-1(E)-octene.

18. The alkene of claim 1, wherein said alkene is methyl N-acetyl-S-3-[(3R,4S)-1-phenyl-4-hydroxy-4,8-dimethylnona-1(Z)-7-dienyl]-(R)-cysteinate.

19. The alkene of claim 1, wherein said alkene is (5RS,6SR)-9,9-dimethoxy-6-hydroxy-6-methyl-1-phenyl-5-phenylthio-(1E,3Z)-nonadiene.

20. The alkene of claim 1, wherein said alkene is (5R,6S)-5-benzylthio-6-hydroxy-1-phenyl-10-(2-tetrahydropyranyloxy)-(1E,3Z)-decadiene.

21. The alkene of claim 1, wherein said alkene is (5R,6S)-5-benzylthio-6,10-dihydroxy-1-phenyl-(1E,3Z)-decadiene.

22. The alkene of claim 1, wherein said alkene is (5R,6S)-5-benzylthio-6-hydroxy-1-phenyl-10-(2-tetrahydroxypyranyloxy)-(1E,3E)-decadiene.

23. The alkene of claim 1, wherein said alkene is (5R,6S)-5-benzylthio-6,10-dihydroxy-1-phenyl-(1E,-3E)-decadiene.

24. The alkene of claim 1, wherein said alkene is (3R,4S)-1-phenyl-3-phenylthio-4-hydroxy-4,8-dimethyl-nona-1(Z), 7-diene.

25. A method for the treatment of inflammation in a mammal which comprises administering to the mammal a pharmaceutical composition which comprises a pharmaceutically-effective amount of an alkene of claim 1 in association with a pharmaceutically-acceptable diluent or carrier.

26. A pharmaceutical composition for the treatment of an allergic reaction in a mammal which comprises an anti-allergy effective amount of an alkene of claim 1 in association with a pharmaceutically-acceptable diluent of carrier.

27. A method for the treatment of an allergic reaction in a mammal which comprises administering to the mammal, the composition of claim 26.

* * * * *